(12) United States Patent
Atkins et al.

(10) Patent No.: US 6,726,482 B2
(45) Date of Patent: Apr. 27, 2004

(54) TOOTH WHITENING MEANS

(75) Inventors: Don C. Atkins, Los Alamitos, CA (US); Garry Tsaur, 19222 Transbarger St., Rowland Heights, CA (US) 91748; Steve Bortz, Westlake Village, CA (US)

(73) Assignee: Garry Tsaur, Rowland Heights, CA (US)

( * ) Notice: Subject to any disclaimer, the term of this patent is extended or adjusted under 35 U.S.C. 154(b) by 19 days.

(21) Appl. No.: 10/097,521

(22) Filed: Mar. 13, 2002

(65) Prior Publication Data

US 2003/0175657 A1 Sep. 18, 2003

(51) Int. Cl.$^7$ ................................................ A61C 5/00
(52) U.S. Cl. ...................................................... 433/215
(58) Field of Search ....................... 433/215, 80; 604/1, 604/2, 3; 401/132, 196; 606/162

(56) References Cited

U.S. PATENT DOCUMENTS 3,757,782 A * 9/1973 Aiken ............................ 604/3
6,500,408 B2 * 12/2002 Chen ............................ 424/53
6,517,350 B2 * 2/2003 Diasti et al. ................. 433/215
2003/0103913 A1 * 6/2003 Nathoo ......................... 424/53

* cited by examiner

Primary Examiner—Kevin Shaver
Assistant Examiner—Melba Bumgarner
(74) Attorney, Agent, or Firm—Joe Nieh

(57) ABSTRACT

The present invention is a tooth whitening means utilizing a simple and economical process of whitening and polishing teeth that does not require assistance or application by a professional such as a dentist. The present invention comprises of a cotton swab applicator with one or more absorbent tip and a hollow body which contains the liquid activating agent of the tooth whitening compound and a tooth whitening compound in the form of a solid powder wherein the liquid activating agent is released into the absorbent tip of the cotton swab applicator and allowed to contact the solid powder tooth whitening compound which is then applied to the surfaces of the tooth with the absorbent tip of the cotton swab applicator to whiten and polish the tooth.

12 Claims, 1 Drawing Sheet

TOOTH WHITENING MEANS

BACKGROUND-FIELD OF INVENTION

The present invention relates to a simple and economical process of whitening and polishing teeth that does not require assistance or application by a professional such as a dentist.

DESCRIPTION OF RELATED ART

Teeth become stained over time from contact with coffee, tea, juice, tobacco, and other foods. Currently, there are three basic methods to remove this layer of stain and whiten the teeth. The first method requires one or more visit to a dentist's office and have the teeth professionally cleaned by a dentist. The second method uses an at-home bleaching kit that the user can apply at home. The third method uses whitening toothpastes and slowly whitens teeth over time with regular brushing of the teeth with the whitening toothpaste.

The first method is the most expensive but is the most effective. A chairside bleaching requires one or more visits to a dentist's office. Each visit may take from 30 minutes to one hour. During the chairside bleaching, the dentist will apply either a protective gel to the gum or a rubber shield to protect the oral soft tissues. A bleaching agent is then applied to the teeth. Some procedures may use a special light, such as a laser light, to enhance the action of the agent. This first method requires taking time off from work or regular daily activity to schedule one or more appointments with a dentist, travel to the dentist's office, and remain there for 30 minutes to one hour for the procedure, assuming there are no waiting, and paying a large sum of money for the procedure.

The second method is more economical than visits to a dentist's office. The user may purchase an at-home bleaching kit over-the-counter from the local pharmacy or drug store to perfume the whitening procedure himself at home. These products contain peroxides to actually bleach the tooth enamel. Most of these products rely on percent carbamide peroxide as the bleaching agent. Carbamide peroxide is generally available is several different concentrations such as 10%, 16%, and 22%. These products typically come in the form of a gel and are placed in a mouthguard. The actual application process varies. Some products are used for about twice a day for 2 weeks, and others are intended for overnight use for one to two weeks. A dentist may provide a custom-fitted mouthguard if the at-home bleaching kit is purchased from the dental office. This method has various side effects that may bother the user. The teeth can become sensitive during the period when the user is using the bleaching solution. Some user may experience soft tissue irritation-either from a mouthguard that doesn't fit properly or from solutions that may come in contact with the tissue. Furthermore, the whitening effect from this method is gradual and requires constant contact with the bleaching agent for hours at a time. This method also requires a delicate procedure of applying the bleaching agent in a generic mouth guard and inserting that mouthguard into the user's mouth for hours at a time. If the mouth guard is not custom fitted by a dentist, which is an expensive procedure, the mouth guard may be very uncomfortable to wear. Furthermore, a generic mouthguard may irritate the gum if improperly fitted.

The third method is the least effective but may be the least expensive. All toothpaste help remove surface stains through the action of mild abrasives. Some "whitening" toothpastes have special chemical or polishing agent that provide additional stain removal effectiveness. However, this method is the least effective and requires daily use over extended period of time.

SUMMARY OF THE INVENTION

The present invention is a tooth whitening means utilizing a simple and economical process of whitening and polishing teeth that does not require assistance or application by a professional such as a dentist. The present invention comprises of a cotton swab applicator which contains the liquid activating agent of the tooth whitening compound in its hollow body and the tooth whitening compound in the form of a solid powder wherein the liquid activating agent is released into the cotton swab applicator tip and allowed to contact the solid powder tooth whitening compound which is then applied to the surfaces of the tooth with the cotton swab applicator to whiten and polish the tooth.

The liquid activating agent may comprise of pure water or may comprise of a solution of glycerin and artificial or natural flavoring in the water in a predetermined ratio. The tooth whitening compound comprises of a mixture of magnesium peroxide and aluminum oxide in a predetermined ratio.

DETAILED DESCRIPTION OF THE PREFERRED EMBODIMENT

Figure 1:
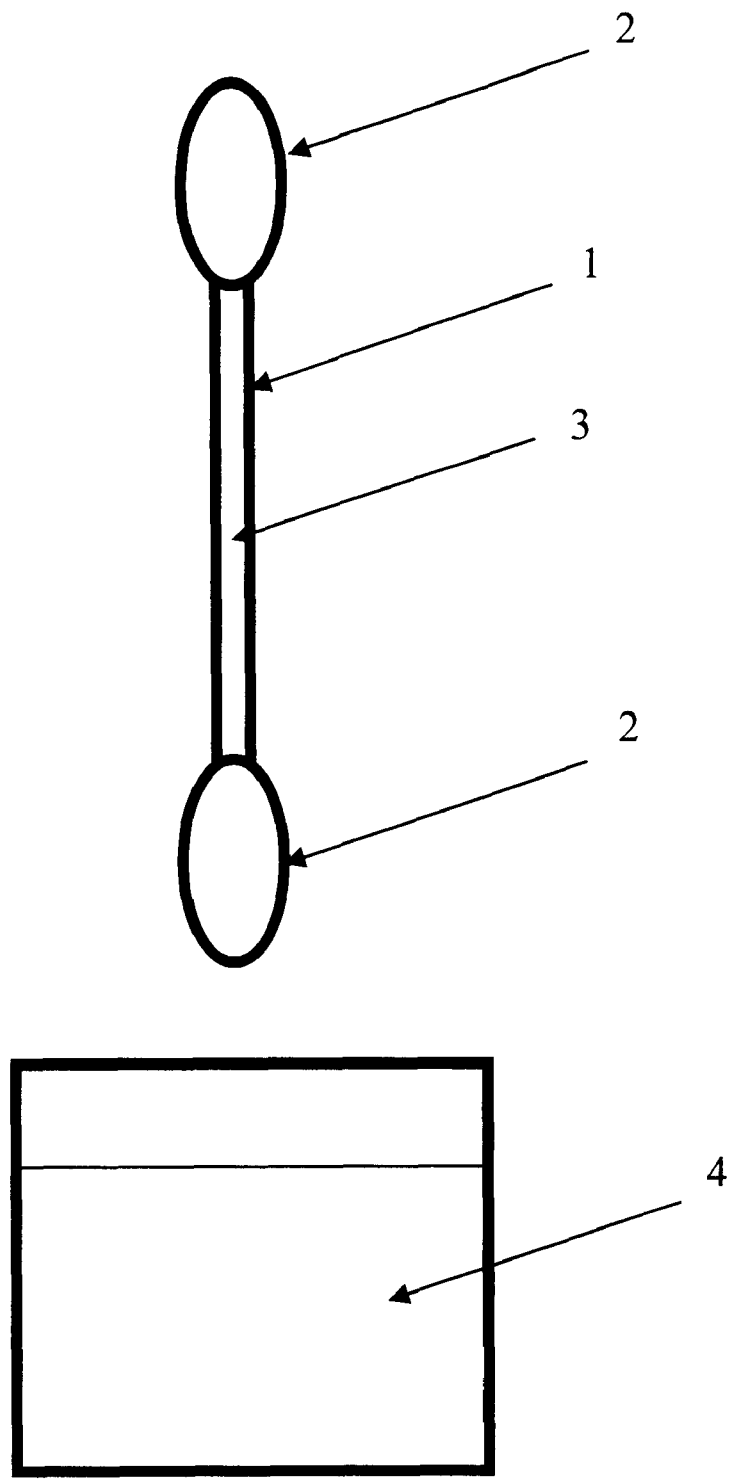
FIG. 1 shows the preferred embodiment of the present invention.

The preferred embodiment of the tooth whitening means comprises of a common cotton swab applicator with a hollow tube housing 1 with one or two absorbent tips 2 attached to one or both ends of the hollow tube housing 1 wherein the hollow tube housing 1 contains an activator 3 in the form of a liquid which will interact with the tooth whitening compound 4 in the form of a solid powder. The preferred embodiment of the present invention utilizes the cotton swab applicator manufactured and sold by Swabplus, Inc. in Pomona, Calif., USA, but any other design of the cotton swab applicator that allows the liquid activator 3 to be contained in the hollow tube housing 1 and subsequently released into the absorbent tips 2 may be utilized.

The liquid activator 3 in the hollow housing 1 may be water, de-ionized water, or a solution of water and an aqueous compatible ingredient such as glycerin that will prolong the contact time of the tooth whitening compound 4 and offset the diluting effect of the saliva. In the preferred embodiment of the present invention the solution contains 50 percent water, 49.9 percent glycerin, and 0.1 percent artificial or natural flavoring.

The tooth whitening compound 4 is a mixture of a solid peroxide with aluminum oxide. In the preferred embodiment of the present invention, the tooth whitening compound 4 is a mixture of magnesium peroxide and aluminum oxide in the ratio of 85 percent magnesium peroxide and 15 percent aluminum oxide. The magnesium peroxide is the oxidizer that whitens the tooth and the aluminum oxide is the polish that cleans and polishes the surfaces of the tooth.

When the liquid activator 3 in the hollow housing 1 is released into and absorbed by the absorbent tip 2 of the cotton swab applicator the absorbent tip 2 becomes saturated with the activator 3. By placing the saturated absorbent tip 2 of the cotton swab applicator in physical contact with the tooth whitening compound 4 powder, the saturated absorbent tip 2 picks up the tooth whitening compound 4 and the activator 3 in the absorbent tip 2 reacts with the tooth whitening compound 4 and activates the magnesium peroxide. This activated tooth whitening compound is then rubbed onto the surfaces of the tooth to whiten and polish the surfaces of the tooth. The activated magnesium peroxide oxidizes the stain and whitens the tooth while the aluminum oxide acts as a polish to clean the surfaces of the tooth and polish the surfaces of the tooth to a smooth shiny surface. All the ingredients in the present invention are safe for humans.

The present invention has the advantages of being very low cost and does not require professional application. The small head of the applicator allows for easy maneuverability within the confined cavity of the mouth and will reach all surface areas of every tooth. The tooth whitening means is quick and easy to apply and will have positive results in just 7 to 24 days depending on the severity and the type of stains. After each cleaning, the surfaces of the tooth are left with a very smooth and shinny surface.

What is claimed is:

1. A tooth whitening means comprising:
   an activator in the form of a liquid contained in a hollow housing of a cotton swab applicator with one or more absorbent tip; and
   a tooth whitening compound in the form of a solid powder;
   wherein after said liquid activator is released into the absorbent tip of the cotton swab applicator, the absorbent tip with the liquid activator is placed in contact with the solid powder of the tooth whitening compound to activate the tooth whitening compound and the activated tooth whitening compound is then applied to the surface of the tooth with the cotton swab applicator to whiten and polish the tooth surface.

2. A tooth whitening means as in claim 1, wherein the activator is water and wherein the tooth whitening compound is a mixture of magnesium peroxide and aluminum oxide in predetermined ratio.

3. A tooth whitening means as in claim 1, wherein the activator is a solution of an aqueous compatible ingredient that will prolong the contact time of the tooth whitening compound and offset the diluting effect of the saliva in water in predetermined ratio and wherein the tooth whitening compound is a mixture of magnesium peroxide and aluminum oxide in predetermined ratio.

4. A tooth whitening means as in claim 1, wherein the activator comprises glycerin, artificial or natural flavoring, and water and wherein the tooth whitening compound is a mixture of magnesium peroxide and aluminum oxide in predetermined ratio.

5. A tooth whitening means comprising:
   an activator comprising approximately 49.9 percent by weight of glycerin and approximately 0.1 percent by weight of artificial or natural flavoring in approximately 50 percent by weight of water in the form of a liquid contained in a hollow housing of a cotton swab applicator with one or more absorbent tip; and
   a tooth whitening compound comprising a mixture of magnesium peroxide and aluminum oxide in predetermined ratio in the form of a solid powder;
   wherein after said liquid activator is released into the absorbent tip of the cotton swab applicator, the absorbent tip with the liquid activator is placed in contact with the solid powder of the tooth whitening compound to activate the tooth whitening compound and the activated tooth whitening compound is then applied to the surface of the tooth with the cotton swab applicator to whiten and polish the tooth surface.

6. A tooth whitening means as in claim 2, 3, 4, or 5, wherein the ratio of the mixture is approximately 85 percent by weight magnesium peroxide and approximately 15 percent by weight aluminum oxide.

7. A tooth whitening method comprising the steps of:
   releasing an activator in the form of a liquid contained in an hollow housing of a cotton swab applicator with one or more absorbent tip into the absorbent tip of the cotton swab applicator;
   placing the absorbent tip with the activator in contact with a tooth whitening compound in the form of a solid powder to activate the tooth whitening compound; and
   applying the tooth whitened compound to the surface of the tooth with the absorbent tip of the cotton swab applicator;
   wherein the surface of the tooth is whitening and polished by the tooth whitening compound.

8. A tooth whitening method as in claim 7, wherein the activator is water and wherein the tooth whitening compound is a mixture of magnesium peroxide and aluminum oxide in predetermined ratio.

9. A tooth whitening method as in claim 7, wherein the activator is a solution of an aqueous compatible ingredient that will prolong the contact time of the tooth whitening compound and offset the diluting effect of the saliva in water in predetermined ratio and wherein the tooth whitening compound is a mixture of magnesium peroxide and aluminum oxide in predetermined ratio.

10. A tooth whitening method as in claim 7, wherein the activator comprises glycerin, artificial or natural flavoring, and water and wherein the tooth whitening compound is a mixture of magnesium peroxide and aluminum oxide in predetermined ratio.

11. A tooth whitening method comprising the steps of:
    releasing an activator comprising approximately 49.9 percent by weight glycerin and approximately 0.1 percent by weight artificial or natural flavoring in approximately 50 percent by weight water in the form of a liquid contained in an hollow housing of a cotton swab applicator with one or more absorbent tip into the absorbent tip of the cotton swab applicator;
    placing the absorbent tip with the activator in contact with a tooth whitening compound comprising a mixture of magnesium peroxide and aluminum oxide in predetermined ratio in the form of a solid powder to activate the tooth whitening compound; and
    applying the tooth whitening compound to the surface of the tooth with the absorbent tip of the cotton swab applicator;
    wherein the surface of the tooth is whitened and polished by the tooth whitening compound.

12. A tooth whitening method as in claim 8, 9, 10, or 11, wherein the ratio of the mixture is approximately 85 percent by weight magnesium peroxide and approximately 15 percent by weight aluminum oxide.

* * * * *